(12) United States Patent
Rattner et al.

(10) Patent No.: US 6,202,360 B1
(45) Date of Patent: Mar. 20, 2001

(54) MEDICAL WORK STATION WITH DEVICES DISPOSED IN A DOUBLE CEILING OR A DOUBLE FLOOR OF AN OPERATING ROOM

(75) Inventors: Manfred Rattner, Grossenseebach; Bernd Malter, Effeltrich, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/252,918

(22) Filed: Feb. 19, 1999

(30) Foreign Application Priority Data

Feb. 20, 1998 (DE) .............................. 198 07 243

(51) Int. Cl.⁷ .................................... E04F 19/04
(52) U.S. Cl. .................. 52/36.4; 52/220.6; 52/220.8; 52/234; 312/209; 312/223.1; 312/245
(58) Field of Search .................. 52/36.1, 36.2, 52/36.4, 27–29, 64, 220.1, 220.6–8, 243.1, 234, 236.1, 238.1, 239; 312/209, 223.1, 223.5, 223.6, 246, 242, 245; 174/48, 49; 433/50, 77

(56) References Cited

U.S. PATENT DOCUMENTS

| | | | |
|---|---|---|---|
| 4,993,683 | * | 2/1991 | Kreuzer .................. 248/639 |
| 5,072,906 | * | 12/1991 | Foster .................. 248/122 |
| 5,107,636 | * | 4/1992 | Schindele et al. .......... 52/27 |
| 5,299,338 | * | 4/1994 | Foster .................. 5/658 |
| 5,377,371 | * | 1/1995 | Foster .................. 5/503.1 |
| 5,398,359 | * | 3/1995 | Foster .................. 5/658 |
| 5,455,975 | * | 10/1995 | Foster .................. 5/600 |
| 5,618,090 | * | 4/1997 | Montague et al. ............ 312/209 |

FOREIGN PATENT DOCUMENTS 92 18 373 U    3/1994  (DE) .
OS 197 14 984  11/1997  (DE) .

* cited by examiner

Primary Examiner—Carl D. Friedman
Assistant Examiner—Yvonne M. Horton
(74) Attorney, Agent, or Firm—Schiff Hardin & Waite

(57) ABSTRACT

A medical workstation is contained in an operating room having one or both of a double ceiling and a double floor. The medical devices forming the medical workstation are disposed in the double ceiling or in the double floor, or are distributed so that some are disposed in the double ceiling and some are disposed in the double floor. The devices are thus arranged so as not to present a hinderance to operating personnel in the operating room. A connection unit for the medical devices projects into the operating room from the double ceiling or from the double floor.

5 Claims, 3 Drawing Sheets

MEDICAL WORK STATION WITH DEVICES DISPOSED IN A DOUBLE CEILING OR A DOUBLE FLOOR OF AN OPERATING ROOM

BACKGROUND OF THE INVENTION

1. Field of the Invention

The invention is directed to a medical workstation formed by a number of interconnected medical devices.

2. Description of the Prior Art

Medical workstations of the above type usually have stand-alone units, for example device cabinets, that accept the various medical devices, for example an RF device or an ultrasound device. The applicators belonging to the medical devices, for example a high-frequency scalpel or an ultrasound head, are usually arranged in the proximity of a patient support of the workstation, within reach of, for example, a physician treating a patient lying on the patient bearing device. The connection of the medical devices to the appertaining applicators ensues via connecting lines laid in the treatment room containing the medical workstation.

Such a workstation provided for minimally invasive surgery is disclosed, for example, in German Utility Model 92 18 373. The workstation has a mobile apparatus cabinet placed immediately next to a patient support of the workstation, the medical devices required for the operation being accepted in this mobile device cabinet. The workstation is also provided with a patient connection panel that is connected to the medical devices in the device cabinet via a supply conduit and to which applicators of the medical devices can be connected.

It has proven disadvantageous that such a device cabinet in known workstations generally occupies space, with only limited space being available in the treatment room containing the workstation. Particularly if the device cabinet is disposed directly next to the patient support, the cabinet presents a hinderance since it limits the space needed for the freedom of movement and action of a physician during the treatment of a patient.

SUMMARY OF THE INVENTION

It is an object of the present invention to provide a medical workstation of the type initially described wherein the medical devices can be arranged in a room containing the workstation so that the space for movement and action required, for example, by a physician for the treatment of a patient is not restricted.

According to the invention, this object is achieved in a medical workstation having medical devices that are disposed in a double ceiling and/or in a double floor of a room containing the workstation. The medical devices of the inventive workstation are thus no longer arranged in a device cabinet that occupies space, for example, in a treatment or operating room, but in a double ceiling and/or in a double floor of the treatment or operating room. In this way, the devices are removed from the movement and action space of, for example, a physician or an operating team and do not limit the movement and action space in the treatment of a patient. The devices also can be partly or even completely (i.e., not visible from the outside) integrated into the double ceiling or into the double floor. The devices can be arranged only in the double floor, only in the double ceiling or both in the double floor as well as in the double ceiling.

In one version of the invention the workstation has at least one connection unit connected to the medical devices and projecting from the double ceiling or from the double floor into the room. This connection unit is provided with connections for the applicators and/or operating and/or display devices belonging to the medical devices. The connection unit for the applicators and/or operating and/or display devices of the medical devices offers the advantage that none of the applicators of the individual medical devices or the operating and display devices must be respectively directly connected to the corresponding medical devices, but simply can be connected to this connection unit, that is preferably arranged so as to be easily accessible in the room and favorable in location with reference to the patient on the patient support mechanism. The connection unit usually requires little space and is thus barely a disturbing factor in the treatment of a patient. Different connection units can be provided for different device groups of medical devices. For example, separate connection units can be provided for anesthesia devices and for surgical devices, respectively.

In another version of the invention, the connection unit and the medical devices form a device center that is displaceable, with the connection unit moving within the room and the medical devices moving in the double ceiling or in the double floor. In this way, the device center can be adapted to different treatment situations, i.e. can be positioned in a suitable way relative to a patient to be treated who is, for example, on a patient support mechanism, so that a physician can work in a relaxed and comfortable way at the workstation. Long connecting lines between the connection unit and the applicators of the medical devices utilized in the operating site, that are complicated to manipulate in a surgical intervention, thus are avoided. There is also the possibility that, for example, anesthesia devices together with a connection unit form an anesthesia center and surgical and/or diagnostic devices of the workstation together with a further connection unit form a surgery center, both of which are adjustable relative to one another and, for example given a surgical intervention, can be respectively placed relative to a patient support mechanism at locations which are beneficial in view of the type of surgery to be conducted.

In another embodiment of the invention only the connection unit is adjustable relative to the medical devices, namely within the room. In this embodiment of the invention, thus, the medical devices need not be displaced together with the connection unit in order, for example, to make it possible for a physician to work in a comfortable and relaxed way at the workstation. Rather, the medical devices are stationarily arranged and only the connection unit is selectively placed relative to, for example, a patient on a patient support mechanism in conformity with a treatment situation. Connecting lines between the connection unit and the applicators of the medical devices utilized at the operating site that are long and difficult to manipulate thus are avoided.

In a further version of the invention the medical workstation is provided with a system for climate control and/or air circulation in the room containing the workstation, with the components of such a system also being disposed in the double ceiling and/or in the double floor of the room containing the workstation. This embodiment has the advantage that the components for climate control and/or air circulation are arranged outside the motion and action space of, for example, a physician, so that these components do not occupy any space in the room and thus do not have a disturbing effect on the treatment of a patient.

DESCRIPTION OF THE PREFERRED EMBODIMENTS

Figure 1:
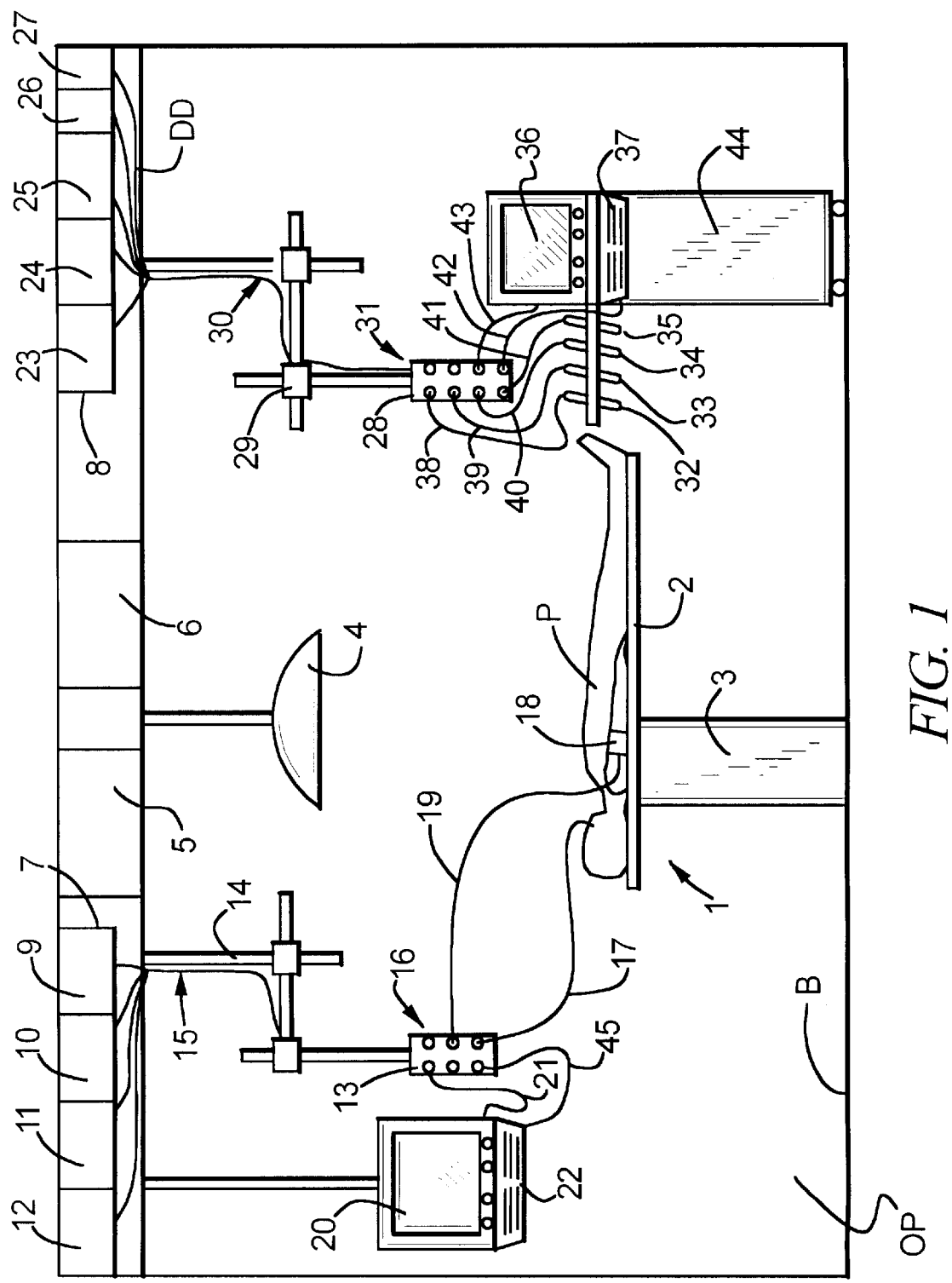
FIG. 1 is a side view of a first embodiment of a workstation in accordance with the invention, wherein devices of the workstation are disposed in a double ceiling of an operating room.

This embodiment of the inventive medical workstation shown in FIG. 1 is a surgical workstation that is located in an operating room OP with a double ceiling DD.

The workstation includes a patient support mechanism in the form of a patient support table 1. The patient support table 1 is provided with a patient support plate 2 arranged on a lifting column 3, a patient B lying thereon in this exemplary embodiment. The lifting column 3 of the patient support table 1 is arranged on the floor B of the operating room OP.

An operating lamp 4 is arranged at the double ceiling DD above the patient bearing table 1.

Inventively, a device 5 for climate control of the operating room OP, a device 6 for circulating air in the operating room OP, and medical devices are arranged in the double ceiling DD.

In the exemplary embodiment, the medical devices are of anesthesia devices arranged in a first device center 7 and surgical and diagnostic devices arranged in a second device 8.

In the exemplary embodiment, a respiration device 9, a device 10 for delivering anesthesia gases, a device 11 for monitoring the body functions of the patient P and a control computer 12 are arranged in the device center 7 provided for the anesthesia devices. The devices 9, 10, 11 are connected to the control computer 12 via a communication bus in a known way that is not shown. A connection unit 13 is allocated to the device center 7, this connection unit 13 being attached to an articulated arm 14 provided with horizontally and vertically adjustable articulations. The connection unit 13 is connected to the devices 9, 10, 11 and to the control computer 12 via connecting lines 15 and is provided with corresponding connectors 16 for applicators, for an operating and display station for the devices 9, 10, 11 and/or for the control computer 12. In the exemplary embodiment, one applicator is a hose conduit 17 having a mask or intubation system (not shown) for respiration and delivery of anesthesia gases to the patient P, that is connected to a corresponding connector 16 of the connection unit 13, which in turn is connected to the respiration device 9 and the device 10 for delivering anesthesia gases. Another application is a cuff 18 attached to the arm of the patient P for determining body functions, for example the blood pressure of the patient P. The cuff 18 is connected via a connecting cable 19 to a connector 16 of the connection unit 13 which is in turn connected to the device 11. Moreover, a monitor 20 and a control panel 22 are connected via connecting cables 21, 45 to respective connectors 16 of the connection unit 13, which are in turn connected to the control computer 12 that controls the devices 9, 10, 11 of the device center 11 and exchanges data with the devices 9, 19, 11. The monitor 20 displays data relating to the anesthesia and the life functions of the patient P, for displaying status information of the devices, 10, 11, 12 and for displaying operating menus of the devices 10, 11, 12 that can be selected via the control panel 22.

In the exemplary embodiment, an RF device 23, an ultrasound device 24, a rinse/suction pump controller 25, a cold light source 26 and a control computer 27 are integrated in the device center 8 provided for surgical and diagnostic devices, the devices 23 through 26 being connected to the control computer 27 via a communication bus (not shown). The control computer 27 has a higher hierarchical ranking than the devices 23 through 26; the control computer 27 exchanges data with the devices 23 through 26 and correspondingly drives them. A connection unit 28 that is attached to an articulated arm 29 provided with horizontally and vertically adjustable articulations is allocated to the device center 8. A connection unit 28 is connected to the devices 23 through 26 and to the control computer 27 via connecting lines 30 and is provided with corresponding connectors 31 for applicators, an operating and display station for the devices 23 through 26 and/or for the control computer 27. In the exemplary embodiment, a high-frequency scalpel 32, an ultrasound head 33, a cold light 34, a rinse/suction applicator 35, a monitor 36 and a control panel 37 are connected via connecting lines 38 through 43 to corresponding connectors 31 of the connection unit 28. Like the control panel 37, the monitor 36 is connected to the control computer 27 via the connection unit 28. The monitor 36 serves for displaying image information of, for example, the ultrasound device 24, for displaying status information and operating menus of the devices 23 through 26 that can be selected via the control panel 37. The applicators 32 through 35, the monitor 36 and the control panel 37 are arranged on a device carriage 44.

In the exemplary embodiment of the inventive medical workstation shown in FIG. 1, thus, the device 5 for climate control of the operating room OP, the device 6 for air circulation in the operating room OP and the medical devices of the device centers 7 and 8 are arranged in the double ceiling DD of the operating room OP and thus are located outside the motion and action space of, for example, an operating team composed of surgeons, anesthesiologists, operating room nurses and operating room attendants during a surgical intervention at the patient P. The connection units 13 and 28 of the device centers 7 and 8 are arranged at the articulated arms 14, 29 so as to be adjustable relative to the patient bearing table 1, or the patient P, so that they can be selectively arranged at locations relative to the patient P that are most beneficial for allowing relaxed and comfortable work of the operating team in the context of the particular operation which is to be conducted.

Figure 2:
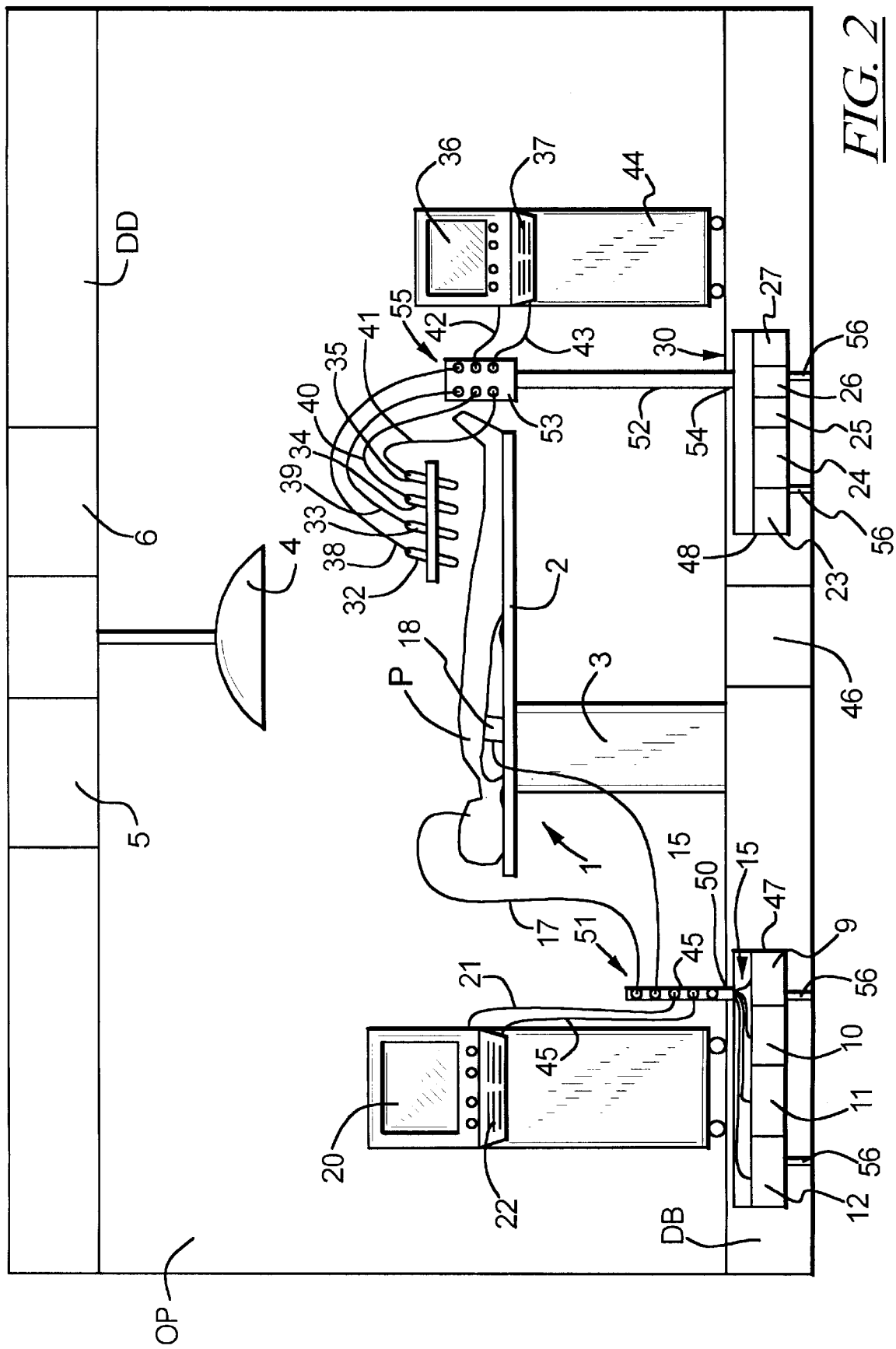
FIG. 2 is a side view of a second embodiment of a workstation in accordance with the invention wherein devices are disposed in a double floor of an operating room.

FIG. 2 shows another embodiment of the inventive medical work station, wherein components of the workstation that are substantially structurally and functionally the same as components of the workstation in FIG. 1 are provided with the same reference numerals.

Differing from the medical workstation shown in FIG. 1, the medical workstation shown in FIG. 2 has a double floor DB in addition to the double ceiling DD. In addition to the device 5 for climate control of the operating room OP integrated in the double ceiling DD, a second device 46 for climate control of the operating room OP is arranged in the double floor DB of the operating room OP.

As in the case of the medical workstation shown in FIG. 1, a device center 47 for anesthesia devices and a device center 48 for surgical and diagnostic devices are provided in the medical workstation shown in FIG. 2, these being arranged in the double floor DB of the operating room OP in the exemplary embodiment.

As in the exemplary embodiment described above, a respiration device 9, a device 10 for delivering anesthesia gases, a device 10 for monitoring the body functions of the patient P and a control computer 12 are arranged in the device center 47 provided for the anesthesia devices, whereby the devices 9, 10, 11 are again connected via a communication bus (not shown) to the control computer 12 that controls the devices 9, 10, 11. A connection unit 49 that projects from the double floor DB into the operating room OP through an opening 50 is arranged at the device center 47. The connection unit 49 is connected to the devices 9, 10, 11 and to the control computer 12 via connecting lines 15 and is provided with connectors 51 for applicators and an operating and display station for the devices 9, 10, 11 and/or for the control computer 12.

As in the exemplary embodiment described above, a RF device 23, an ultrasound device 24, a rinse/suction pump control 25, a cold light source 26 and a control computer 27 are integrated in the device center 48 provided for the surgical and diagnostic devices, the devices 23 through 26 being connected via a communication bus (not shown) to the control computer 27 that controls the devices 23 through 26. A stand 52 for a connection unit 53 that extends through an opening 54 of the double floor DB is arranged at the device center 48. As in the exemplary described above, the connection unit 53 is connected to the devices 23 through 26 and to the control computer 27 via connecting lines 30 and is provided with corresponding connectors 55 for applicators and for an operating and display station for the devices 23 through 26 and/or for the control computer 27. As in the exemplary embodiment described above, a high-frequency scalpel 32, an ultrasound head 33, a cold light 34, a rinse/suction applicator 35, a monitor 36 and a control panel 37 are connected via connecting lines 38 through 43 to corresponding connectors 55 of the connection unit 53.

Figure 3:
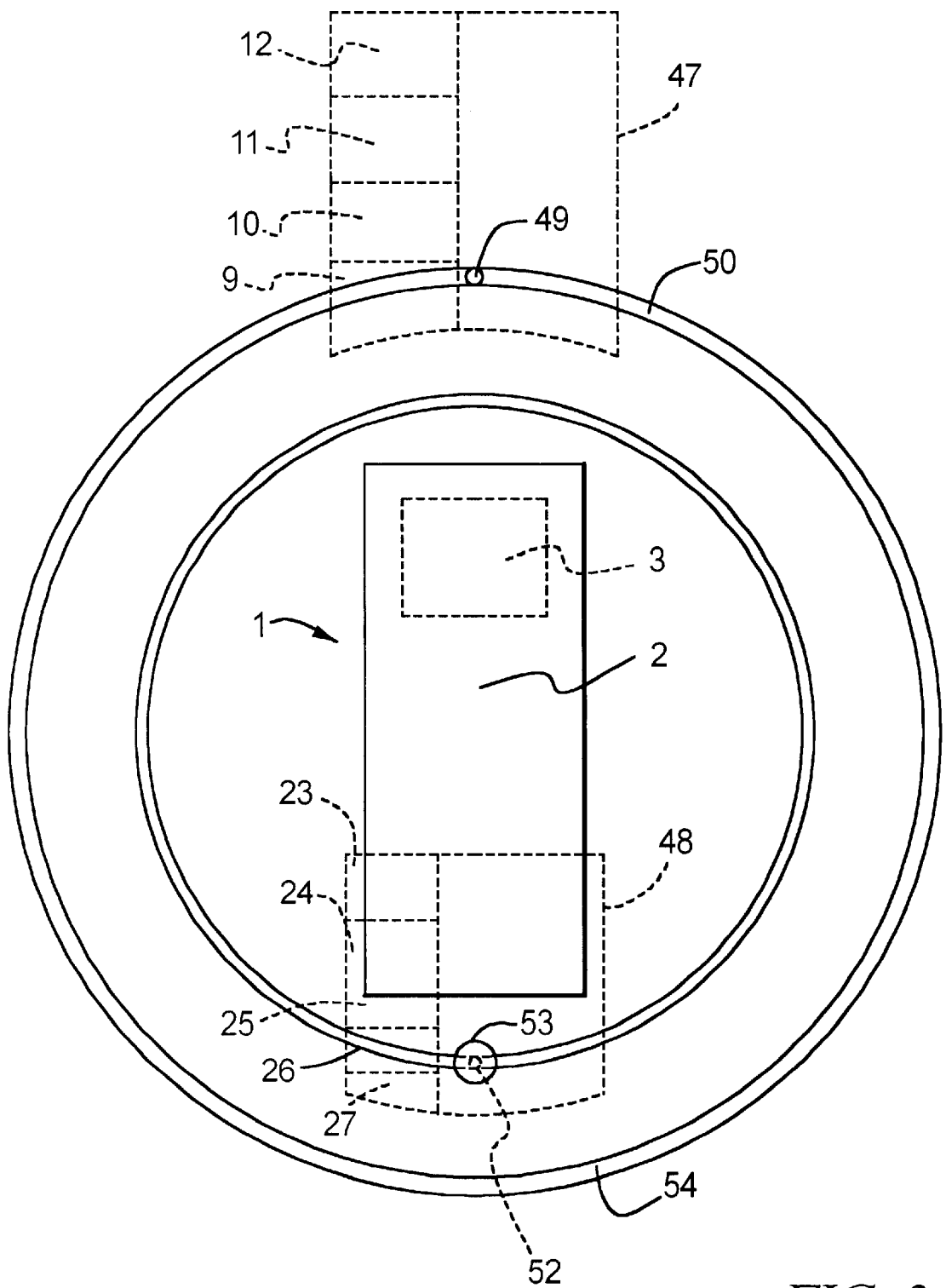
FIG. 3 is a schematic view from above of a portion of the second embodiment of the workstation of FIG. 2.

In the exemplary embodiment of FIG. 2, the device centers 47, 48 of the medical devices are provided with wheels 56, so that they are displaceable on the wheels 56 in the double floor DB. Given displacement movements of the device centers 47, 48, the connection units 49, 53 move within the operating room OP as the device centers 47, 48 move in the double floor DB. In a schematic view from above, FIG. 3 shows a part of the workstation of FIG. 2. FIG. 3 shows that, in the exemplary embodiment, the openings 50, 54 are annular openings through which the connection unit 49 or the stand 52 of the connection unit 53 extends. The connection units 49, 53 of the device centers 47, 48 are thereby adjustable along the annular openings 50, 54, as the device centers 47, 48, rigidly connected to the connection units 49, 53, are moved. Whereas the connection units 49, 53 move within the operating room OP, the movement of the device centers 47, 48 takes place in the double floor DB. The device centers 47, 48 in the exemplary embodiment are implemented such that they are conducted past one another on circular paths and cannot collide with one another.

In the exemplary embodiment of FIG. 2, the devices 5, 46 for the climate control of the operating room OP, the device 6 for air circulation in the operating room OP, and the medical devices of the device centers 47, 48 are arranged outside the motion and action space of an operating team working at the medical workstation, and thus do not restrict the action and motion space of the operating team during a surgical procedure.

The above exemplary embodiments of the inventive workstation are only described as an example and are not the only ways of implementing the invention. Within the context of the invention, for example, it is possible to form mixed versions of any type of the workstations shown in FIGS. 1 and 2.

Thus, for example, the medical devices of the workstation shown in FIG. 1 can also be arranged in a double floor DB and the connection unit can be arranged, for example, at a holding mechanism adjustable at the double floor DB that is adjustably mounted at the wall or at the patient support table 1. The holding mechanism need not be an articulated arm or arranged at a displaceable holder, for example a carriage.

Further, a number of device centers with medical devices can be arranged in the double floor DB as well as in the double ceiling DD. It is also possible to arrange all of the medical devices in only one device center, or distributed in the double floor DB, as well as in the double ceiling DD.

Moreover, the device centers 47, 48 shown in FIG. 2, or only one of the device centers 47, 48, can be arranged in the double ceiling DD and can be adjustable on wheels in the double ceiling DD, for example as in the case of FIG. 2.

The device centers need not necessarily be displaceable on wheels but can be guided, for example, on rails. The coupling of the device centers to the connection units need not necessarily be mechanically rigid but, for example, can be magnetic. In this way, an adjustment of the connection unit in the operating OP can effect a corresponding adjustment of the device center in the double floor DB, in the double ceiling DD, as a result of the magnetic coupling to the appertaining device center.

The adjustment path of the device centers need not necessarily be circular as in the case of the exemplary embodiment shown in FIG. 2, but can alternatively be elliptical or, when expedient, can proceed on a curved line.

In the case, for example, of the exemplary embodiment shown in FIG. 2, further, the device 6 for air circulation can be arranged in the double floor DB or an additional device for air circulation can be provided in the double floor DB.

Further, a double ceiling DD need not necessarily be present; rather, only a double floor DB can be present wherein the devices provided for climate control and air circulation and the medical devices are correspondingly arranged.

The devices for climate control and/or air circulation of the operating room OP, as well as the medical devices, moreover, need not be completely integrated into the double floor DB, into the double ceiling DD, but can partially project therefrom.

The inventive workstation also need not necessarily simultaneously include devices in the groups of medical devices, devices for climate control and devices for air circulation but can instead include only one or two groups of devices that are arranged in the double floor DB and/or in the double ceiling DD.

Further, the connection unit also need not simultaneously include connectors for applicators and for an operating and display station but can, for example, only have connectors for applicators or a display. Other arbitrary connection combinations are possible.

The operating devices can not only be control panels but can be a joy stick, a track ball, a light pin, a computer mouse or a touch screen.

The inventive workstation has been explained in detail herein with reference to a surgical workstation, however, the inventive medical workstation is not limited to surgery.

The present invention is subject to many variations, modifications and changes in detail. It is intended that all matter described throughout the specification and shown in the accompanying drawings be considered illustrative only. Accordingly, it is intended that the invention be limited only by the spirit and scope of the appended claims.

What is claimed is:

1. A medical workstation comprising:

an operating room having a double structure selected from the group consisting of a double ceiling and a double floor; and a plurality of medical devices disposed in at least one of said double ceiling and said double floor.

2. A medical workstation as claimed in claim 1 wherein at least one of said medical devices has an auxiliary unit selected from the group of an applicator and operating and display station, and wherein said medical workstation further comprises a connection unit having at least one connector for making a connection to said auxiliary unit, and a mount for said connecting unit projecting from said double structure.

3. A medical workstation as claimed in claim 2 wherein said connection unit is connected to a group of medical devices in said plurality of medical devices, said group of medical devices being fewer in number than said plurality of medical devices, and wherein said group of medical devices is movable within said double structure and wherein said connection unit is co-movable in said operating room together with said group of medical devices.

4. A medical workstation as claimed in claim 2, further comprising an adjustable mount for said connection unit allowing selected positioning of said connection unit within said operating room.

5. A medical workstation as claimed in claim 1, further comprising at least one additional device selected from the group of devices consisting of a climate control device and an air circulation device, and wherein said at least one additional device is disposed in at least one of said double ceiling and said double floor.

* * * * *